(12) United States Patent
Boggett et al.

(10) Patent No.: US 6,263,227 B1
(45) Date of Patent: Jul. 17, 2001

(54) APPARATUS FOR IMAGING MICROVASCULAR BLOOD FLOW

(75) Inventors: David Boggett, Axminster; Xiabing Huang, Somerset, both of (GB)

(73) Assignee: Moor Instruments Limited, Devon (GB)

( * ) Notice: Subject to any disclaimer, the term of this patent is extended or adjusted under 35 U.S.C. 154(b) by 0 days.

(21) Appl. No.: 09/194,111

(22) PCT Filed: May 21, 1997

(86) PCT No.: PCT/GB97/01388

§ 371 Date: Jan. 19, 1999

§ 102(e) Date: Jan. 19, 1999

(87) PCT Pub. No.: WO97/43950

PCT Pub. Date: Nov. 27, 1997

(30) Foreign Application Priority Data

May 22, 1996 (GB) .................................... 9610700

(51) Int. Cl.$^7$ ...................................................... A61B 5/05
(52) U.S. Cl. ........................ 600/407; 600/473; 600/476; 356/39
(58) Field of Search .................................... 600/407, 473, 600/475, 476, 477, 310, 504; 356/39, 337, 345, 341, 346, 319–320; 250/356.1, 363.01, 370.08

(56) References Cited

U.S. PATENT DOCUMENTS

| 5,961,466 | * | 10/1999 | Anbar | ..................................... 600/474 |
| 6,006,128 | * | 12/1999 | Izatt et al. | ............................ 600/476 |

* cited by examiner

Primary Examiner—Brian L. Casler
(74) Attorney, Agent, or Firm—Barry R. Lipsitz; Douglas M. McAllister

(57) ABSTRACT

An apparatus for measuring and imaging blood perfusion in tissue comprises a monochromatic laser light source, means for shaping the laser light beam, means for irradiating a section of the surface of the tissue with the laser light beam, means for collecting light scattered from the irradiated section, an image sensor comprising a plurality of photodetectors, each photodetector of the sensor being able to receive collected light from a predetermined sub area of the section of the tissue surface and produce a corresponding electrical output signal linearly related to the detected instananeous laser light intensity; means for processing the electrical output signals from the plurality of photodetectors, means for calculating the average Doppler frequency shift for each sub area from which scattered light is detected, means for producing an image of the blood perfusion in the tissue section irradiated from the processed output signals, and an image display means. The apparatus enables fast tissue blood perfusion image to sub second times.

21 Claims, 6 Drawing Sheets

APPARATUS FOR IMAGING MICROVASCULAR BLOOD FLOW

The present invention relates to an apparatus for the measurement and imaging of particle movement and flow in fluids, particularly for the measurement and imaging of blood flow in the small superficial blood vessels of body tissue.

Blood flow in the small blood vessels of the skin performs an essential role in the regulation of the metabolic, hemodynamic and thermal state of an individual and the condition of the microcirculation over both long and short time periods can reflect the general state of health. The degree of blood perfusion in the cutaneous microvascular structure often provides a good indicator of peripheral vascular disease and reduction of blood flow in the microcirculatory blood vessels can often be attributed to cutaneous vascularisation disorders; so there are many situations in routine clinical medicine where measurement of the blood flow is important.

The microcirculation, its responses to stimuli, and its response to therapeutic regimes, were not open to routine continuous assessment and investigation until the introduction of the laser Doppler technique in the 1970's and subsequent developments in the 1980's.

The technique depends on the Doppler principle whereby laser light which is incident on tissue, typically the skin surface, is scattered by moving red blood cells and undergoes frequency broadening. The frequency broadened laser light, together with laser light scattered from static tissue, is photodetected and the resulting photocurrent processed to provide a signal which correlates with blood flow.

Perfusion measurements using single and multiple channel fibre optic laser Doppler monitors have been made on practically all tissues and applied in most branches of medicine and physiology. The technique and its application has been described in numerous publications. A representative selection of these are included in 'Laser—Doppler Blood Flowmetry', ed. A. P. Shepherd and P. Å. Oberg, Kluwer Academic Publishers 1990 and also 'Laser Doppler', ed. G. V. Belcaro, U. Hoffmann, A. Bollinger and A. N. Nicolaides, Med-Orion Publishing Co. 1994.

The application of these principles to measurements in the microcirculation was described by M. D. Stern in Nature Vol 254, 56, March 1975, 'In vivo evaluation of microcirculation by coherent light scattering'; M. D. Stern et al 1977 'Continuous measurement of tissue blood flow by laser 'Doppler spectroscopy' Am J. Physiol 232: H441–H448; and subsequently in U.S. Pat. No. 4,109,647.

For some clinical applications, such as plastic surgery and wound healing, point measurements using optic probes attached to the skin are severely limited and this has prevented widespread application in these areas. Three reasons for this are: point to point variation (spatial variability) requiring several readings to give reliable measurement, contact between the probe and the tissue surface, and interference from fibre movements which degrade the measurements.

These problems have been mainly overcome by the development of laser Doppler scanners which map perfusion over an area of tissue, typically 100 cm$^2$ and in some cases over 1000 cm$^2$, using a scanning laser beam and one or more photodetectors. EP-A-0282210 describes an apparatus for monitoring blood stream in the skin surface which employs a linear sensor comprising a plurality of light receiving elements to receive the laser light reflected by the skin surface, memory means for storing the output signals from the light receiving elements and calculating means for processing these signals to derive information about the blood stream. The blood stream velocity or distribution information may thereby be calculated and displayed. WO90/11044 describes a method of determination of blood flow and an apparatus for use therein which involves projecting a beam of laser light to move over a surface beneath which blood flow in a vessel or vascular bed is to be determined, collecting the reflected and scattered light, measuring a spectrum of frequencies in the collected light and determining from differences in the frequencies the blood flow beneath the surface under examination. WO91/06244 describes a system which includes means for directing a laser beam onto a body part to be examined and guided movement of the laser beam through a series of measurement points over the body part in accordance with a predetermined scanning pattern. The laser beam is halted at each measurement point for a given time interval. These devices have found many research applications and have generated considerable clinical interest.

The present invention seeks to significantly reduce imaging times, in some circumstances to sub second times, and provide means to record video and blood perfusion images of the same tissue site simultaneously.

In the present invention provision can be made in the apparatus to switch between two or more monochromatic laser light sources of different wavelengths to enable laser Doppler blood flow measurements to be made sequentially at the different wavelengths.

The differences between measurements at different wavelengths provides information on flows at different depths below the tissue surface and information on tissue and blood absorption of light for the different wavelengths.

In the present invention provision can be made in the apparatus to irradiate the tissue surface simultaneously with monochromatic laser light of different wavelengths and simultaneous detection of light scattered from the tissue at the two or more laser light wavelengths using a similar number of image sensors and suitable optical filters.

The magnitude of a blood perfusion measurement, commonly termed 'flux', which is proportional to the product of average red blood cell speed and red blood cell concentration in an element of the volume of tissue sampled, is dependent amongst other factors on the imager/tissue surface distance.

Provision can be made in the apparatus to measure the distance using either a CCD camera video image or an intensity photo image recorded using the image sensor and compensate in the image processing for the distance dependence.

The present invention provides an apparatus for measuring and imaging blood perfusion in tissue comprising
  a monochromatic light source;
  means for shaping the laser light beam;
  means for irradiating a section of the surface of the tissue with the laser light beam;
  means for collecting light scattered from the irradiated section;
  an image sensor comprising a plurality of photodetectors, each photodetector of the sensor being able to receive collected light from a predetermined sub area of the section of the tissue surface and produce a corresponding electrical output signal linearly related to the detected instantaneous laser light intensity;
  means for processing the electrical output signals from the plurality of photodetectors to produce processed output signals comprising;

measurements of the power spectrum of the photocurrents generated in the detection of laser light scattered from static tissue and Doppler broadened laser light scattered from moving blood cells;

the calculated average Doppler frequency shift for each sub area from which scattered light is detected;

the calculated blood volume concentration for each sub area from which scattered light is detected;

the calculated blood perfusion for each sub area from which scattered light is detected;

measurements of the intensity of the detected scattered light for each predetermined sub area;

means for producing an image of the blood perfusion in the tissue section irradiated from the process output signals; and an image display means.

Compared with the systems disclosed in WO90/11044 and WO91/06244 the present invention provides fast tissue blood perfusion imaging using an image sensor which is either a linear or two dimensional photodetector array for detecting the Doppler shifted and Doppler unshifted scattered laser light, and signal processing done with the aid of large scale digital signal processor integrated circuits processing the multi-channel laser Doppler signals in parallel. The present invention can be used in a scanning or non scanning mode to produce blood perfusion images and/or multi-channel blood perfusion recordings. In the scanning mode the laser beam can be scanned across the tissue surface at a substantially constant speed with measurements made on the fly or stepped across and measurements made with a halted beam.

According to EP-A-0282210 a simple differential calculation is used for analysing speckle pattern to generate blood flow information. Thus the bandwidth of signals processed is severely limited, the measurement results in erroneous evaluation of blood flow in the irradiated tissue, and in addition the calculation does not provide a blood flux measurement.

The present invention has a means to process the full spectrum of photocurrents associated with the detection of scattered laser light from tissue and red blood cells moving in the microcirculation. It provides measurements of a wide spectrum of red blood cell (rbc) speeds, the average rbc speed, measurement of the number concentration of rbcs in each sub section of irradiated tissue, and measurement of rbc flux. Furthermore it enables the combination of the blood perfusion (flux) image with a colour video image of the surface of the tissue. This combination of images, showing and recording the location, colour and anatomical details of the tissue surface under examination together with the blood perfusion image, provide the clinician with a powerful diagnostic instrument.

The array comprising a plurality of photodetectors used in the present invention may be a linear array or a two dimensional array.

Either type of detector array can be used in a non scanning mode i.e. with a fixed area of tissue irradiated. Using a two dimensional photodetector array enables a relatively large area of tissue blood perfusion to be mapped. Using a linear array the blood perfusion along a well defined line in the tissue surface can be recorded. For both types of detector flow measurements can be made with either single short duration laser light exposure, or repeated exposures or continuous exposure. Short single or repeated exposures have the advantage that the average laser power incident on the tissue surface is reduced compared to continuous exposure and hence higher peak laser powers can be used if necessary. Repeated exposures and continuous exposure enable multiple measurements to be made from each sub area of tissue enabling temporal variations of blood flow to be recorded in addition to the spatial variations.

Both types of detector array can be used in a scanning mode with either measurements made with the area or line of irradiation moving across the tissue surface and measurements made on the fly, or with the laser beam stepped across the tissue surface and measurements made with the beam halted. The laser beam movements can be produced by a rotating mirror or beam splitter or by direct rotation of the laser beam shaping means.

With a two dimensional array the area of tissue that can be mapped, without moving the beam or tissue surface positions, depends on a number of factors but in particular the laser power density on the tissue surface, the number of photodetector elements in the array, and the desired spatial resolution for the measurements (the distance separating centres of adjacent sub areas of tissue). The time taken to measure the blood perfusion and compute the blood perfusion map, for a given number of photodetector elements depends mainly on the bandwidth of the photocurrents processed, the desired frequency resolution, and the calculating speed of the signal processors used and the number used in parallel processing. Sub second frame rates are achievable for a 64×64 element array.

For a 16×16 element photodetector array and a spatial resolution of the tissue sub areas of between 2 to 3 mm, the measurement area for a non scan mode of operation is about 40×40 $mm^2$. Larger areas can be mapped by increasing the number of array elements or reducing the spatial resolution, assuming that the detected laser power per element enables an acceptable signal to noise ratio to be achieved for the detected signals.

The tissue area being mapped requires illumination with laser light to a sufficiently high power density to achieve the required signal to noise. For efficient use of the laser light power a relatively uniform power distribution is needed over the irradiated tissue area; however conventional beam expanding optics results in an approximate Gaussian power distribution resulting in a large fraction of the irradiated area being illuminated with low intensity light. An embodiment of the present invention uses a simple, inexpensive means of shaping a collimated laser beam, or a diverging beam from a laser diode, to produce a circular cross section diverging beam which has approximately uniform power distribution over more than half the beam width. The beam shaping means is a length of multi-mode optic fibre which has a high numerical aperture into which the laser light is focused at one end. The emitted diverging beam at the end has the characteristics described. The shaped laser beam is directed at the target area by simply pointing the fibre end in the appropriate direction.

Two dimensional photodetector arrays, which are suitable for the multi-channel laser Doppler measurements performed by the apparatus of this present invention, can have a high cost. Suitable linear photodetector arrays can cost significantly less and can be used in place of a two dimensional array for some blood perfusion measurements. In general too there are fewer photodetector elements in the array so that the required laser power for the illuminating beam is less.

In the present invention when a linear photodetector is used the tissue surface is illuminated with a line of laser light with separation of half power points across the line width typically 0.5 mm to 1.0 mm.

The beam diverges from the optical line generator lens so that the effective line length on the tissue surface depends on the lens/tissue surface distance. To ensure acceptable signal to noise for the detected signals in one embodiment of the present invention, and resolutions of between 1.0 mm to 2 mm, line lengths are limited to approximately 90 mm if a 64 element photodiode is used. Typical line rates of 10 Hz or higher are achievable.

Repeated measurements with a fixed beam position enables temporal records of blood flow changes to be recorded for as many points along the line of laser light irradiation as there are elements in the array.

Scanning the line across the tissue surface in a step mode enables measurements to be made for a large area of tissue in a matter of a few seconds. Mapping times of approximately 6 seconds for a 64×64 pixel image have been achieved with one embodiment of the present invention.

In a simple optical line generator the basic optical components are a collimator and a cylindrical lens which converts a beam with a pencil shaped beam cross section to a diverging beam with a line cross section and with a Gaussian power distribution profile along its length. A more uniform power distribution is preferred to make efficient use of laser power and reduce power dependent signal variations.

In one embodiment of the present invention, a commercially available line generator is used, which generates a line which is uniform in power within approximately ±10% over approximately 80% of its length.

The means for irradiating a section of the surface of the tissue with monochromatic light includes means for shaping the laser beam, and includes means for directing the laser beam onto a section of the tissue surface to be examined; preferably by reflection from a hot mirror if near infra-red laser radiation, or a beam splitter if visible laser radiation or a combination of visible and near infra-red laser radiation. A mirror or beam splitter also provides a means for moving the beam over the said tissue surface in accordance with a determined scanning pattern. The means for scanning the laser beam over the tissue surface in a predetermined pattern includes a means for determining and recording the position of the beam at any point of the scan and means for halting the beam at a predetermined position or positions during the scan. If the apparatus is intended for use in a non scan mode only, the laser beam can be shone directly onto the tissue surface.

The means are typically a dc servo motor or stepper motor together with high resolution shaft encoders to provide accurate and reliable means to monitor the reflection position and hence the position of the laser radiation on the tissue surface.

For rapid scanning of the beam a constant speed mode of scanning can be used with measurements made on the fly. This avoids the need to allow a mirror settling time for each measurement though some noise due to movement artefact is introduced and some low Doppler shift frequency information is lost. The mechanical scanning means is preferably a dc servo motor with Proportional, Integral and Differential control (PID) of mirror angular speed and position using standard control algorithms and systems. Angular speeds of the order of 5 rev/min are typically used for a fast scan.

Laser light scattered by the tissue is preferably reflected from the hot mirror, if near infra-red laser light, or from the beam splitter, if visible laser light, and is then imaged onto the photodetector array typically via an objective lens. For an apparatus intended for use in a non scan mode a cold mirror can be used to reflect visible light and transmit near infra-red.

Each of the photodetectors of the array receives reflected and scattered light from a particular sub section of the section of tissue examined. By processing the signals from all the detectors in the array a one dimensional or two dimensional image of blood perfusion in the tissue section can be produced.

The means for irradiating a section of the surface of the tissue with two or more monochromatic laser light sources of substantially different wavelength in sequence includes a means for selecting a laser wavelength for irradiating the tissue surface and a means for switching between laser outputs of different wavelengths. These means are preferably an electronically controlled optic fibre switch with the number of input optic fibres corresponding to the number of laser light sources used, and one common output fibre. Some laser sources emit useful laser light power at two or more significantly different wavelengths. If the powers and wavelengths are suitable for the laser Doppler measurements such a laser can be used without recourse to an optic fibre switch.

The means to irradiate a section of the system of the tissue surface simultaneously with laser light of two or more significantly different wavelengths comprises a suitable laser or laser sources and a means to combine the outputs of two or more lasers which is preferably an optic fibre coupler with the number of input fibres corresponding to the number of sources used, and one common output fibre.

The multi-wavelength laser light can be shone via beam shaping optics directly onto the tissue surface for an apparatus designed for non scan mode operation only, or via a front silvered mirror or a beam splitter for an apparatus that is intended for operation in a scan or non scan mode.

Where the multi-wave light is a combination of visible and near infra-red and is shone directly onto the tissue surface a cold mirror is preferred as the means to both filter visible from near infra-red and reflect the scattered laser light onto the photodiode arrays. Filtering of infra-red light of one wavelength from infra-red of another wavelength, and visible from visible, is done with band pass optic filters.

Embodiments of the invention will now be described with reference to the accompanying drawings in which.

Figure 1:
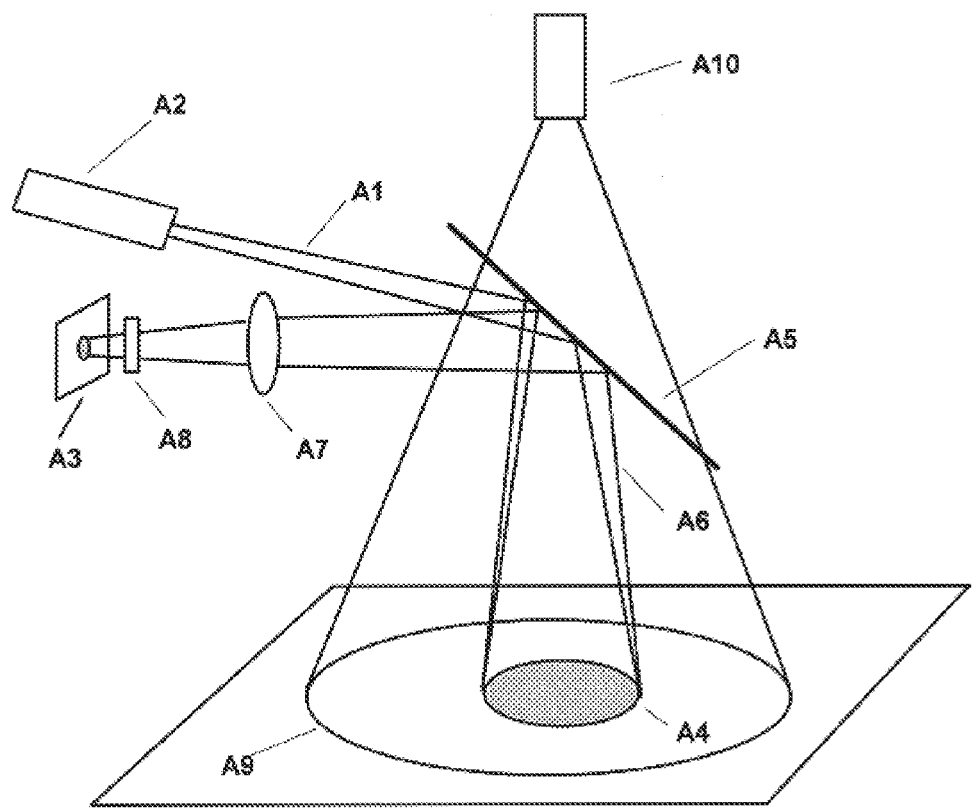
FIG. 1 is an outline schematic drawing of an example of an imager using a 2-D photodetector array which can be operated in scanning or non-scanning mode.
Figure 4:
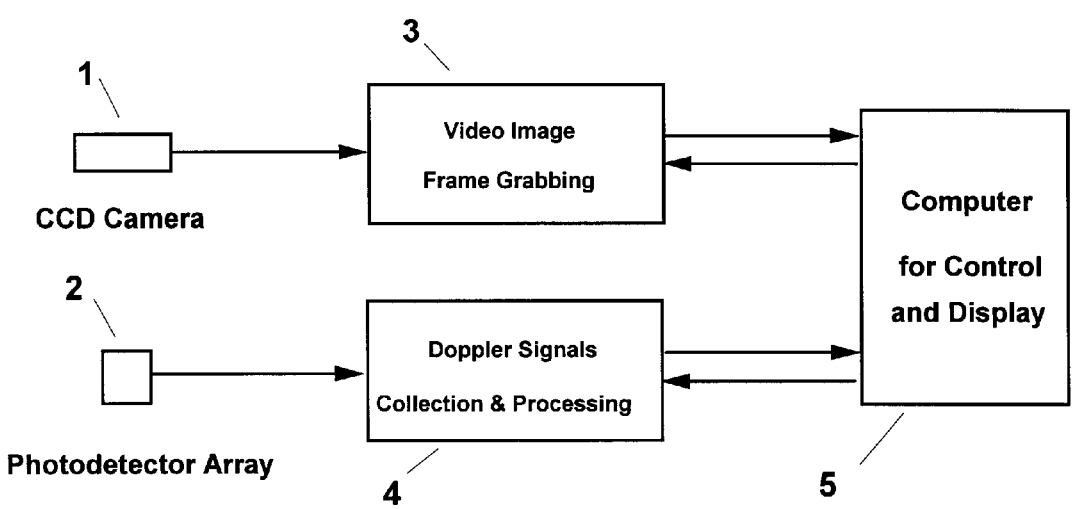
FIG. 4 is a block diagram of a blood perfusion image and video image processing and display system employed in an embodiment of the present invention.
Figure 5:
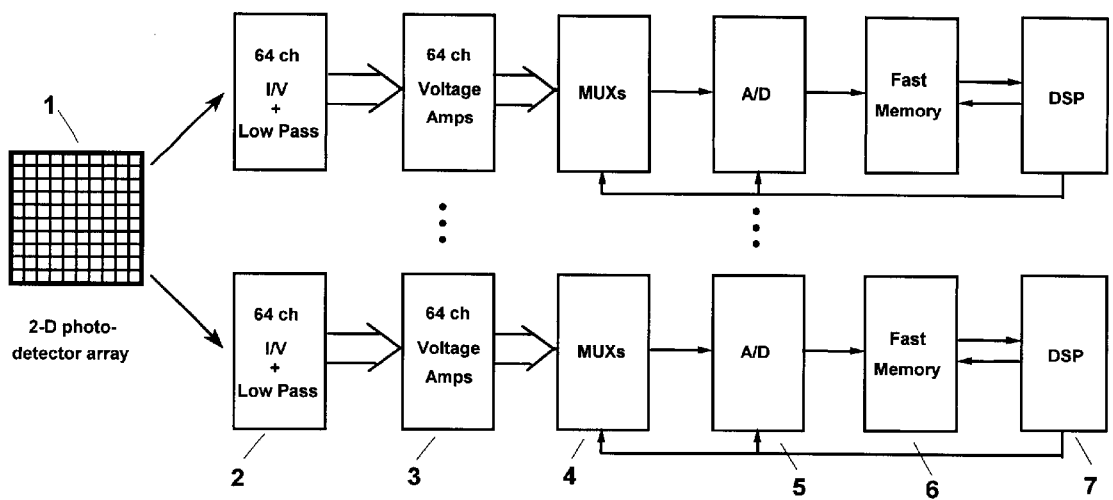
FIG. 5 is a block diagram of a laser Doppler signal collection and processing unit employed in an embodiment of the present invention.
Figure 8:
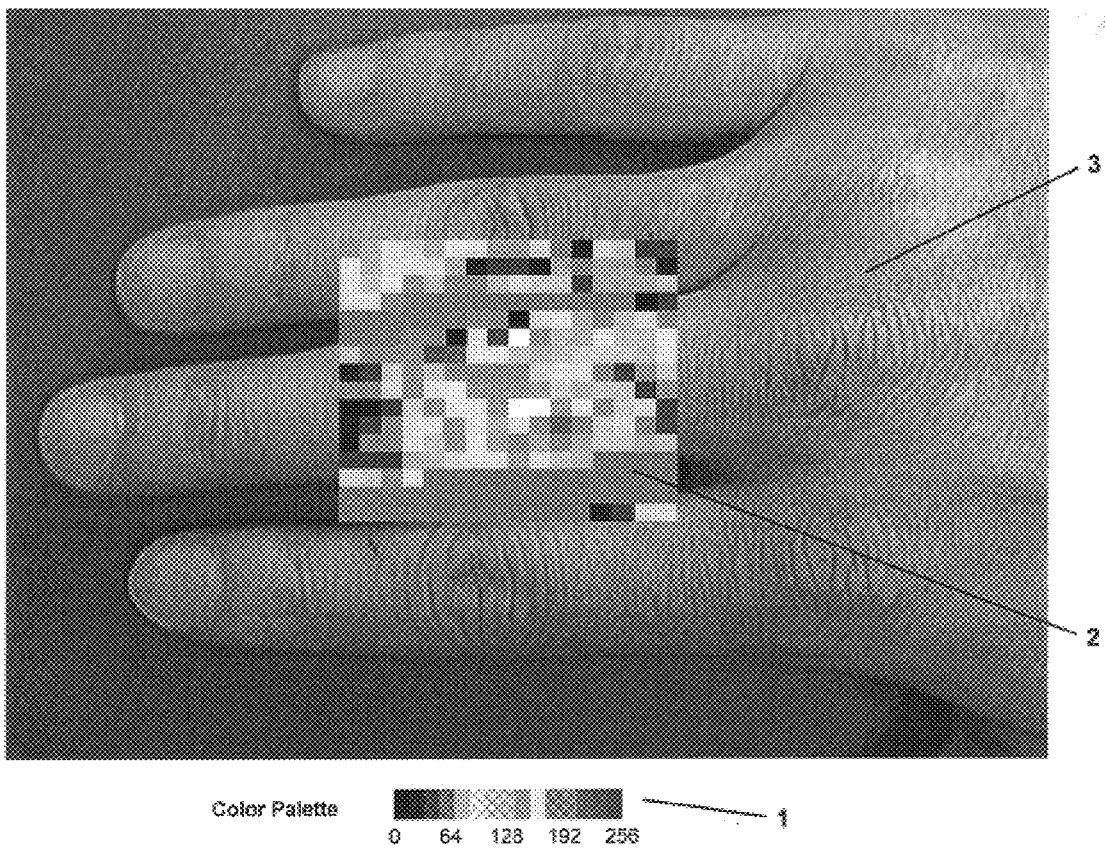
FIG. 8 shows an example of blood perfusion image and video image using the 2-D apparatus of the present invention.

FIG. 1 is a perspective view showing schematically an embodiment of the fast perfusion imaging with simultaneous video imaging according to the invention. A beam of light (A1) from a low noise stable high coherence near infra-red laser or visible laser, with suitable optics to produce a diverging beam (A2), is reflected from a mirror (A5), which is a hot mirror for infra-red laser radiation or a beam splitter for visible laser radiation, and projected onto a section of tissue surface (A4). The hot mirror (A5) has the characteristics of high reflectance for infra-red and high transmission for visible. The beam splitter (A5) is typically a 70/30 type (70% reflection, 30% transmission). Laser light (A6) reflected and scattered by the section of tissue surface is reflected again by the hot mirror or beam splitter (A5) and is then imaged onto the photodetector array (A3) via an objective lens (A7) and an optical band pass filter (A8). Meanwhile, visible light reflected by the large section of tissue surface (A9) is transmitted through the hot mirror or beam splitter (A5) and is imaged on a CCD camera (A10). By means of laser Doppler signal processing (FIG. 4) and video image frame grabbing (FIG. 5), both blood perfusion image and live video image can be displayed on the monitor simultaneously. Since the photodetector array (A3) only images a part (A4) of the tissue surface (A9) being imaged by the CCD camera, it is very useful to locate the perfusion image by superimposing the blood perfusion image on the video image (FIG. 8).

FIG. 4 shows:

a CCD camera (1);

a photodetector array (2);

video image and frame grabbing (3);

Doppler signals collection and processing (4); and

Computer for control and display (5).

To scan the beam across the tissue surface the mirror is rotated and its position controlled by the means described earlier.

Figure 3:
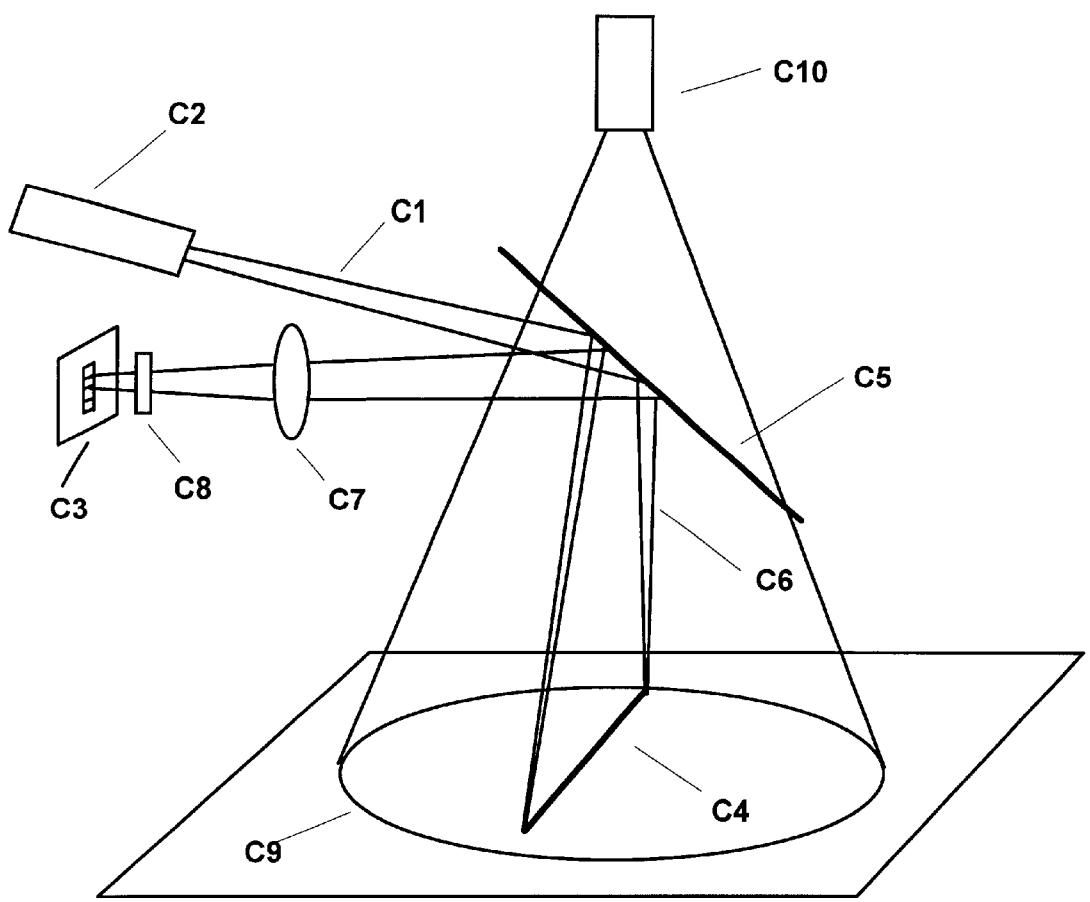
FIG. 3 is an outline schematic drawing of an example of an imager using a 1-D (linear) photodetector array which can be operated in scanning or non-scanning mode.

FIG. 3 is a perspective view of an apparatus similar to that illustrated in FIG. 1 except that the apparatus has a means to irradiate the tissues surface with a laser line beam (C1, C4).

FIG. 3 shows:

a beam of light (C1) from a low noise stable high coherence near infra-red or visible laser, with suitable optics to produce a diverging beam (C2);

a linear photodetector array (C3);

a tissue surface (C4);

a mirror surface or beam splitter (C5);

laser light (C6) reflected and scattered by the section of the tissue surface;

an objective lens (C7);

an optical band pass filter (C8);

a large section of tissue surface (C9); and a CCD camera (C10).

Figure 2:
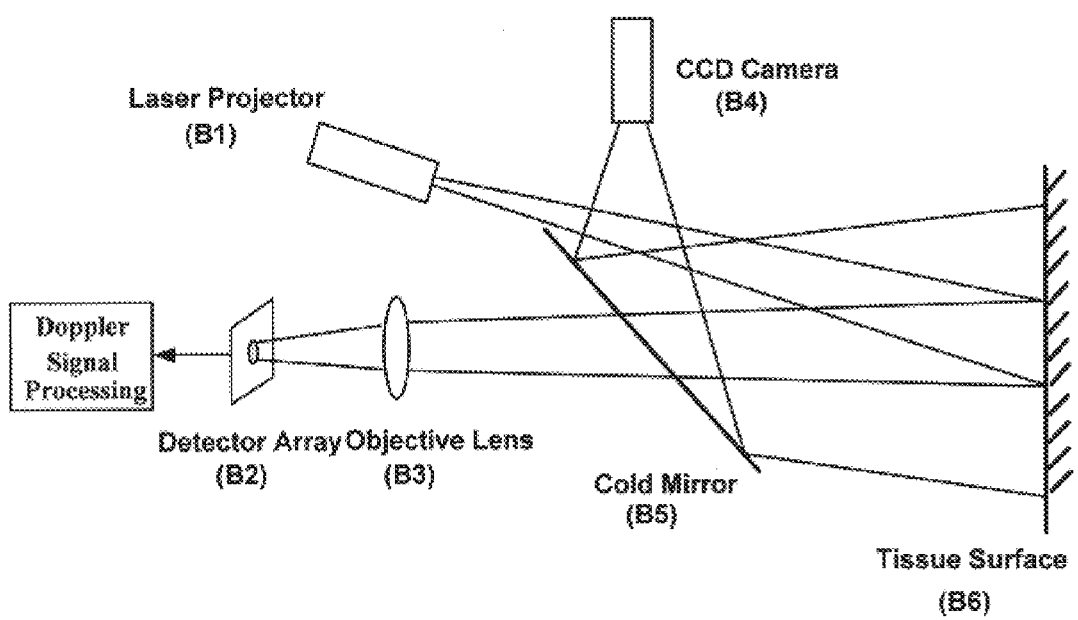
FIG. 2 is an outline schematic drawing of an example of non-scanning apparatus using a 2-D photodetector array.

An alternative embodiment of the imaging system, intended for non scan mode operation, is illustrated in FIG. 2 where the laser light from the projector (B1) is shone directly onto the tissue surface (B6) without the aid of a mirror or beam splitter. For near infra-red laser light irradiation of the tissue surface the scattered light is transmitted through a cold mirror (B5) and imaged onto the detector array (B2) by an objective lens (B3). Additional optical filtering can be provided if necessary with a band pass filter positioned in front of the array. To video image the tissue surface at the same time as recording the blood perfusion image, the surface is illuminated with white light and the scattered light reflected from the cold mirror to the CCD camera (B4). For visible laser light irradiation of the tissue surface the cold mirror is replaced by a beam splitter, typically a 70% transmission 30% reflection type.

All three embodiments of the imager can be operated as multi-wavelength imagers with the different laser sources selected sequentially. If both visible and near infra-red laser sources are used a beam splitter is used to enable perfusion and video images to be recorded at the same time.

Another alternative embodiment not illustrated of the imaging system uses a low noise stable high coherence visible laser light in place of the near infra-red laser and a front silvered mirror, having high reflectance for the visible laser light, in place of the hot mirror. The front silvered mirror is mounted in a mechanism which enables it to be moved into one of two positions. In one position laser light is reflected to illuminate the tissue site and laser light scatter from the tissue is reflected to the detector optics. In the second mirror position a video image of the tissue site can be viewed and recorded.

Figure 11:
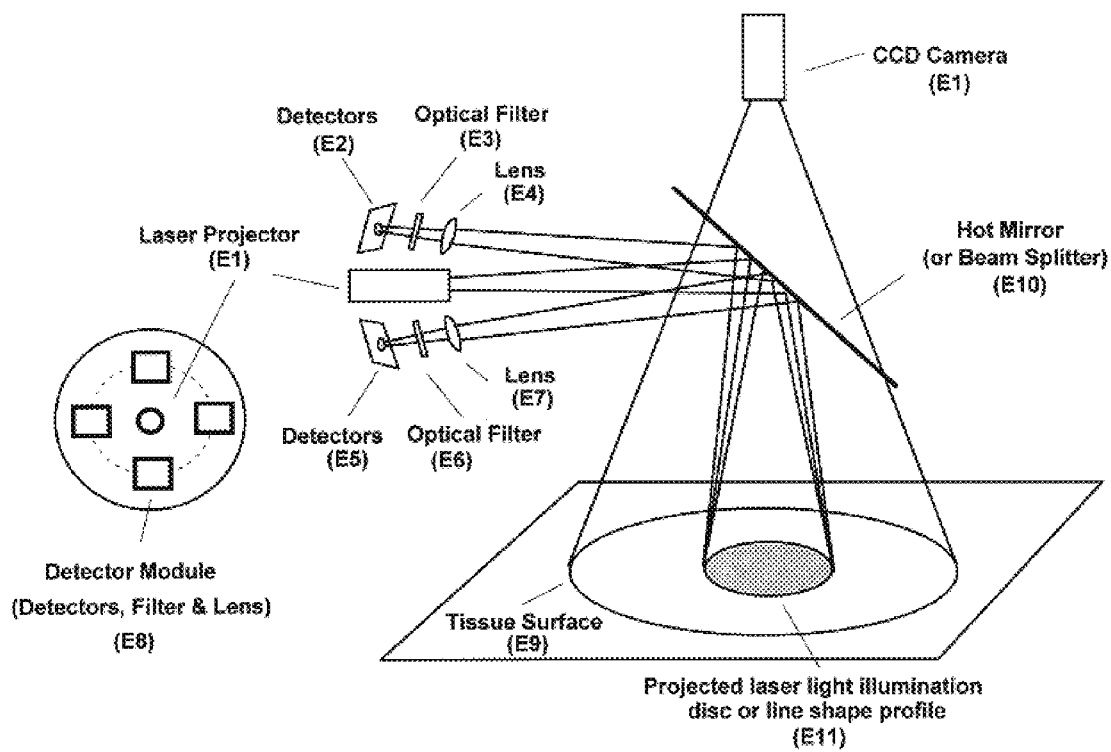
FIG. 11 is an outline schematic drawing of a multi-wavelength imager which can be operated in scanning or non-scanning mode.

FIG. 11 is a perspective view showing schematically an embodiment of a multi-wavelength perfusion imager which has means to irradiate the tissue surface simultaneously with laser radiation of two or more wavelengths derived from one laser projector (E1) or the combined outputs of two or more lasers, and image sensor and optical filtering means (E8) for simultaneously detecting the multi-wavelength scattered light and means for generating separate electrical outputs corresponding to each laser wavelength. This has features similar to the systems illustrated in FIGS. (1) and (3) with the addition of a laser projector (E1) which includes a fibre optic coupler for combining the outputs of two or more lasers. A total of four laser outputs can be combined and used relatively easily with this arrangement.

FIG. 11 shows:

a laser projector (E1);

detectors (E2, E5);

optical filters (E3, E6);

lenses (E4, E7);

a detector module (E8);

the tissue surface (E9);

a hot mirror (E10);

projected laser light illumination disc or line shape profile (E11); and a CCD camera (E12).

The imager illustrated in FIG. 11 can be used in either scan or non scan mode with either a hot mirror, if the laser wavelengths are all infra-red, or a beam splitter if the laser wavelengths are a combination of visible and infra-red.

Figure 10:
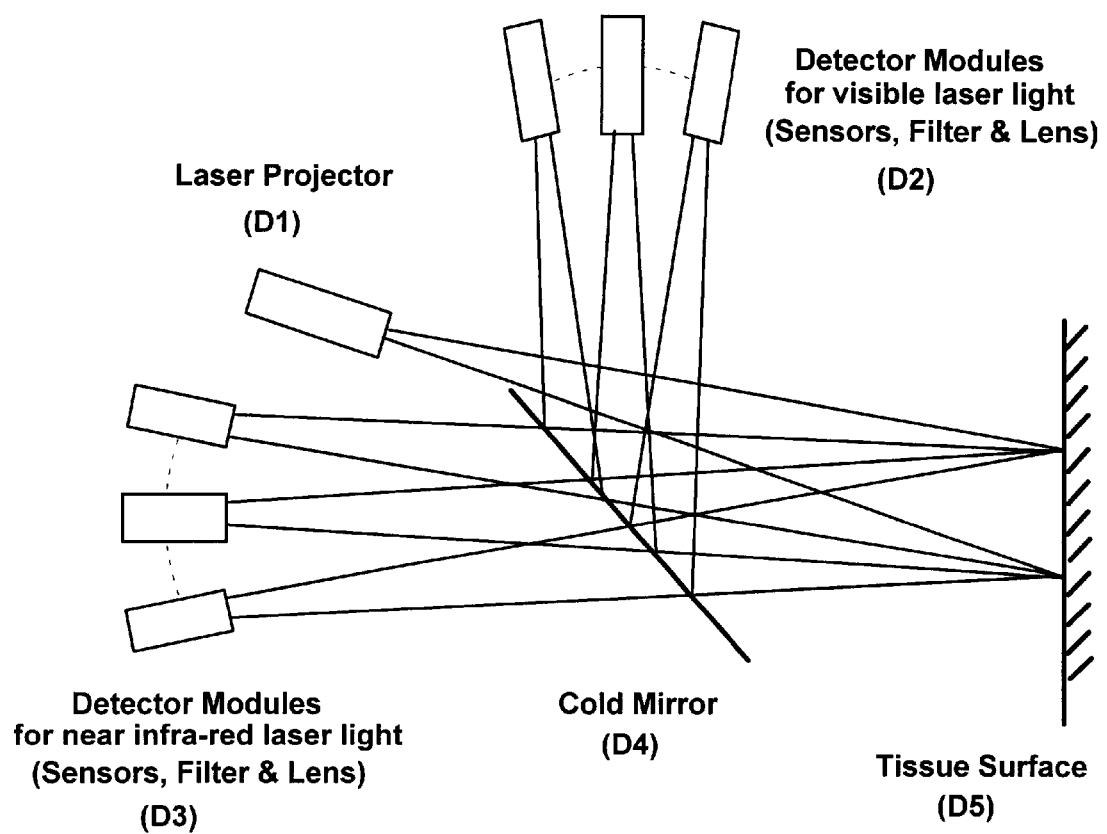
FIG. 10 is an outline schematic drawing of a non-scanning apparatus for a multi-wavelength imager in which visible and near infra-red scattering light is separated by a cold mirror.

FIG. 10 is a drawing of an alternative embodiment of a multi-wavelength imager which is intended for operation in non scan mode only. The combined visible/near infra-red light scattered from the tissue is filtered by the cold mirror (D4). The infra-red is transmitted to detector arrays (D3) and the visible light reflected to detector arrays (D2).

FIG. 10 shows:

a laser projector (D1);

detector modules for visible light (sensors, filter and lens) (D2);

detector modules for near infra-red laser light (sensors, filter and lens) (D3);

a cold mirror (D4); and the tissue surface (D5).

Imaging of a grid of lines printed on card, or a light generated grid, with both the CCD and photodetector array enables a co-ordinate system common to both video and flux images to be established. Standard computing techniques can then be used to superimpose the flux image on the video image. True colour recording of the video image is possible if the tissue surface is illuminated with a suitable white light source.

Laser light reflected and scattered from tissue consists of two fractions, one of which is unchanged in frequency and the other of which has a Doppler broadened fraction due to interactions with moving blood cells in the microvasculature of the tissue. The apparatus of the present invention is provided with means for processing the electrical signals, i.e. blood flow related signals, generated by the plurality of photodetectors in the array and means for producing an image of the blood perfusion in the tissue being examined from these processed signals. In conventional analogue processing techniques, the photocurrent is converted to a voltage, amplified and filtered with an appropriate weighting function (a $\omega^{1/2}$). A measure of blood flow through the tissue can be obtained by squaring and averaging the filtered signals. An alternative approach is to digitise the signal, calculate the FFT, multiply each spectral component by a weighting factor (a $\omega$) and sum all components. The basic algorithm that is implemented to calculate flux values for each channel is:

$$\text{Flux} = \int_{\omega_1}^{\omega_2} \omega P(\omega) d\omega = \sum_{n_1}^{n_2} nP(n)$$

where $\omega=2\pi f$ and f is a Doppler frequency shift. Typical values of $f_1$ and $f_2$ are 20 Hz and 15 KHz espectively.

Each flux measurement will also have dark and shot noise subtracted and will be normalised to account for different laser powers, surface reflectivity and tissue optical absorption.

The analogue processing approach has the advantage of simplicity but needs many more components which makes it very difficult to implement when multi-channel blood flow signals generated by the photodetector array have to be processed in parallel unless a customized integrated circuit is used. Therefore, in the present invention we prefer to process the signals digitally by using large scale digital signal processing (DSP) ICs.

A block diagram (FIG. 5) of the multi-channel Doppler signal collection and digital processing unit, using by way of example a 16×16 photodetector array, illustrates the electronic means of implementing the algorithm for a plurality of detectors. In order to achieve a high frame rate of perfusion imaging, the whole unit comprises 4 processing modules, each amplifying and processing 64 channels of Doppler signals. Output signals from 64 to 256 light receiving elements (1) are converted to voltages and low pass filtered by the I/V and low pass amplifier (2), followed by the voltage amplifier (3) for further increasing the magnitude of the signals. Multi-plexers (4) and a fast A/D converter (5) are employed to convert each channel of analogue signal into digital processing. A DSP (7) is used for data sampling, multi-channel digital signal processing and data communication between the unit and the master system which here is a PC.

Figure 6:
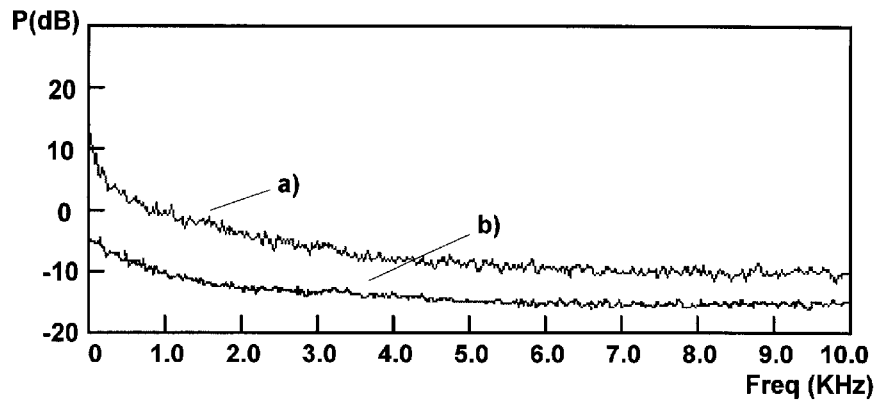
FIG. 6 is two laser Doppler power spectra obtained by examining human skin using the apparatus of the present invention.
Figure 7:
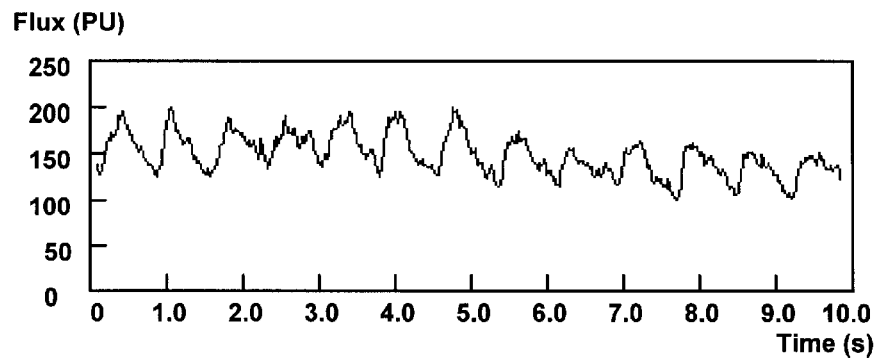
FIG. 7 shows a typical pulse type flux measurement from a fingertip using the apparatus of the present invention.

A fast FFT algorithm using decimation in frequency is utilised in the DSP (7) for flux calculation. For each channel of Doppler signal stored in the memory (6), the time domain digital signals are converted into the frequency domain by the FFT transformation, and then, as explained before, each power spectral component is multiplied by the corresponding number (or frequency) to produce flux output for the corresponding receiving element. FIG. 6 demonstrates two laser Doppler spectra obtained from two sub-areas of the skin tissue by using the present apparatus. The curve a) is the result of high blood perfusion and b) is the power spectrum of low perfusion. FIG. 7 shows a typical pulse type flux output from one of the receiving elements when directing the laser beam onto a finger tip.

By using flux outputs from the plurality image sensor, a two-dimension colour map of blood perfusion can be formed and displayed on a colour monitor. FIG. 8 shows a perfusion image (2) and a video image (3) obtained by using the apparatus of the present invention. Different colours (1) on the image represent 8 different ranges of flux readings. This is a 16×16 blood perfusion image from knuckles superimposed on a colour video image of a whole hand recorded at the same time.

Figure 9:
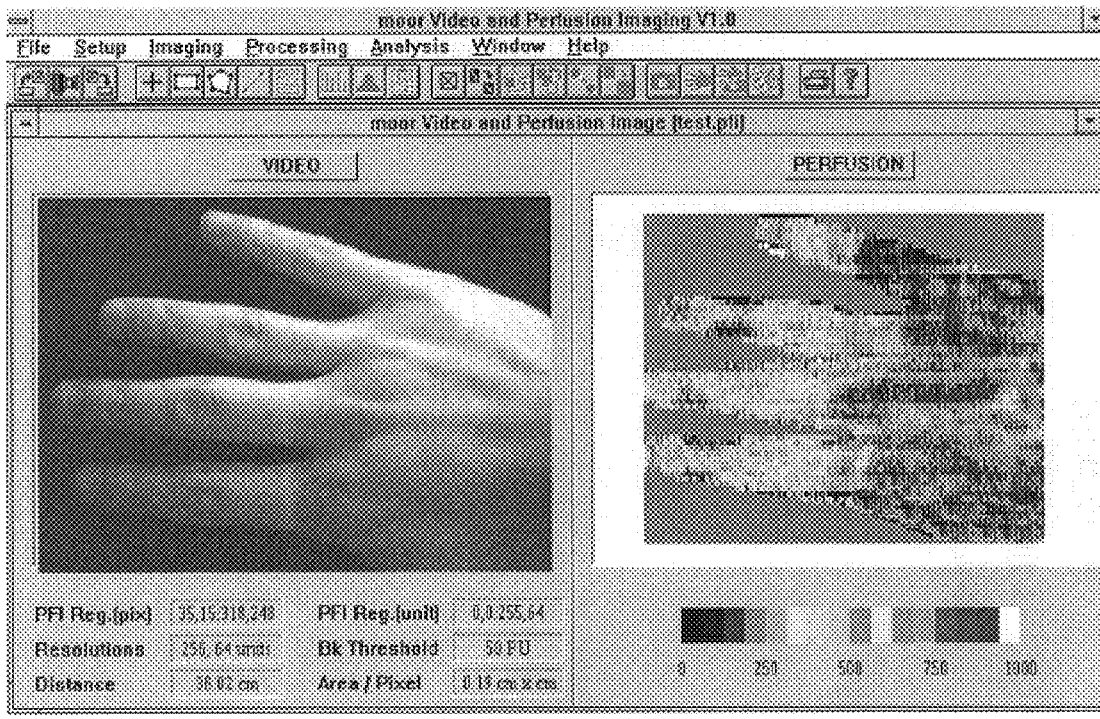
FIG. 9 shows a video image and 256×64 perfusion image of a dorsal surface of a hand using the 1-D apparatus of the present invention.

FIG. 9 shows a perfusion image and a video image obtained by using the embodiment of the apparatus illustrated in FIG. 3 where the linear detector array has 64 photodetectors. The laser line has been scanned in a step mode across the surface of the volunteer's hand in 256 steps to enable a 256×64 blood perfusion measurement to be made for the computation of a 256×64 pixel image.

The perfusion and video images can be displayed separately or with the perfusion image superimposed on the video image. The dc component of the detected laser light can also be displayed as an image, as can the blood volume.

Quantitive information on blood flux, volume and surface reflectivity can be determined from the pixel values using standard numerical processing. Changes due to stimuli can be displayed and measured.

The magnitude of the blood perfusion measurement depends amongst other factors on the distance between the imager and tissue surface, so it is necessary to measure and record this distance. This can be done automatically by imaging with the ccd camera or with the laser beam and photodetector array a simple black and white shape of known dimensions (eg a rectangle) on a card placed on or just in front of the tissue surface. The pixel size of the rectangle from side to side measures the angle subtended at the imager by this side of the rectangle and hence the imager/tissue surface distance can be computed.

A look up table of flux/distance variation can then be used to convert the value of the measured flux to the equivalent value that would have been measured at a standard distance.

What is claimed is:

1. An apparatus for measuring and imaging blood perfusion in tissue, comprising:
   a monochromatic laser light source producing a laser light beam;
   means for shaping the laser light beam;
   means for directing the laser light beam onto a section of tissue surface in order to illuminate said surface section;
   means for collecting light scattered from the illuminated section;
   an image sensor comprising a plurality of photodetectors, each photodetector of the sensor being able to receive collected light from a predetermined sub area of the section of the tissue surface and produce a corresponding electrical output signal linearly related to the detected instantaneous laser light intensity;
   means for processing the electrical output signals from the plurality of photodetectors to produce processed output signals, said processed output signals comprising:

measurements of the power spectrum of the photocurrents generated in the detection of laser light scattered from static tissue and Doppler broadened laser light scattered from moving blood cells;

the calculated average Doppler frequency shift for each sub area from which scattered light is detected;

the calculated blood volume concentration for each sub area from which scattered light is detected;

the calculated blood perfusion for each sub area from which scattered light is detected; and measurements of the intensity of the detected scattered light for each predetermined sub area;

means for producing an image of the blood perfusion, in the tissue section irradiated, from the processed output signals; and an image display means.

2. An apparatus according to claim 1, comprising means for producing images of the blood perfusion in the tissue and means for producing photo images of the tissue surface from the spatial variations of the intensity of the detected scattered laser light.

3. An apparatus according to claim 1 comprising a means for producing images of the blood perfusion in the tissue and means for producing images of the blood volume concentration in the tissue from the processed signals.

4. An apparatus according to claim 1 which additionally comprises a means for producing a video image of the tissue surface which includes the tissue surface irradiated.

5. An apparatus according to claim 4 wherein there is also provided a means for superimposing an image of the blood perfusion on the video image on said display means.

6. An apparatus according to claim 1 wherein signal frequency analysis and calculations of blood flow parameters are done with the aid of large scale digital signal processor integrated circuits processing a large number of channels in parallel.

7. An apparatus according to claim 1 wherein the beam shaping means comprises a length of optic fibre which transmits the laser light to a convenient position within the apparatus and emits the light as a diverging beam having a beam front with relatively uniform intensity.

8. An apparatus according to claim 7 wherein the image sensor has its plurality of photodetectors distributed and fixed in a regular 2 dimensional array.

9. An apparatus according to claim 1 wherein the beam shaping means comprises an optical line generator.

10. An apparatus according to claim 9 wherein the image sensor has its plurality of photodetectors distributed and fixed in a regular one dimensional linear array.

11. An apparatus according to claim 1 with means for optically filtering the collected scattered laser light prior to detection with a band pass filter.

12. An apparatus according to claim 1 comprising additional monochromatic laser light sources having different output wavelengths derived from one or more laser(s) and;

means for selecting a laser wavelength for irradiating the tissue surface;

means for switching between the laser outputs of different wavelengths; and means to compare laser Doppler measurements made with light of different wavelengths.

13. An apparatus according to claim 12 wherein the selecting means and the switching means comprises an electronically controlled optical fibre switch with a number of input optic fibres corresponding to the number of laser light sources used, and one common output optic fibre.

14. An apparatus according to claim 12 comprising means to irradiate the tissue surface simultaneously with one of (a) laser light of two or more wavelengths derived from one laser, or (b) the combined outputs of two or more lasers from a beam combining means, and image sensor and optical filtering means, for simultaneously detecting the multi wavelength scattered laser light and generating separate electrical outputs corresponding to each laser wavelength.

15. An apparatus according to claim 14 wherein the beam combining means is an optic fibre coupler with the number of input fibres corresponding to the number of laser sources used, and one common output fibre.

16. An apparatus according to claim 14 wherein for each of the different laser wavelengths there is a corresponding image sensor each with a suitable band pass optical filter.

17. An apparatus according to claim 16 wherein each sensor means is positioned to one of (a) one side of a beam splitter if a combination of visible and near infra-red laser light is used, or (b) one side of a hot mirror if only near infra-red laser light is used.

18. An apparatus according to claim 16 wherein the means to optically filter scattered visible laser light from scattered near infra-red laser light is a cold mirror.

19. An apparatus according to claim 1 further comprising:

means for scanning a beam of the monochromatic laser light over the tissue surface in a predetermined pattern;

means for scanning the beam at substantially constant speed across the tissue;

means for determining and recording a beam position at any point of the scan;

means for halting the beam at a predetermined position or positions during a scan for predetermined times; and means for making laser Doppler measurements at a predetermined position during a scan.

20. An apparatus according to claim 1 wherein means are provided to measure imager/tissue surface distance, comprising recording a video image of a 2 dimensional shape placed at or close to the tissue surface position and measuring the pixel size of one dimension of the recorded image.

21. An apparatus according to claim 1 wherein means are provided to measure the imager/tissue surface distance, comprising recording a photo image of a 2 dimensional shape and measuring the pixel size of one dimension of the recorded image.

* * * * *